United States Patent [19]

Hardy et al.

[11] Patent Number: 4,845,285

[45] Date of Patent: Jul. 4, 1989

[54] CHEMICAL PROCESS

[75] Inventors: Colin Hardy; Tony R. Martin; Jerzy Czyzewski; Daniel Levin, all of Huddersfield, United Kingdom

[73] Assignee: Imperial Chemical Industries PLC, London, England

[21] Appl. No.: 125,103

[22] Filed: Nov. 25, 1987

[30] Foreign Application Priority Data

Nov. 25, 1986 [GB] United Kingdom ................ 8628109

[51] Int. Cl.$^4$ .......................................... C07C 143/74
[52] U.S. Cl. ....................................... 564/97; 564/95; 564/96; 564/99; 558/424
[58] Field of Search ........................ 564/95, 97, 99, 96; 558/424

[56] References Cited

U.S. PATENT DOCUMENTS

| | | | |
|---|---|---|---|
| 3,856,895 | 12/1974 | Moore et al. | 564/97 |
| 4,005,102 | 1/1977 | Cook et al. | 562/458 |
| 4,285,723 | 8/1981 | Cartwright et al. | 564/99 |
| 4,384,135 | 5/1983 | Cartwright et al. | 562/465 |
| 4,388,472 | 6/1983 | Cartwright et al. | 562/435 |
| 4,589,914 | 5/1986 | Cartwright | 564/95 |
| 4,738,711 | 4/1988 | Barton et al. | 562/474 |

FOREIGN PATENT DOCUMENTS 2103611 2/1983 United Kingdom ................ 564/99

Primary Examiner—Prince E. Willis
Assistant Examiner—Helene Kirschner
Attorney, Agent, or Firm—Cushman, Darby & Cushman

[57] ABSTRACT

A process for preparing a compound of formula (II):

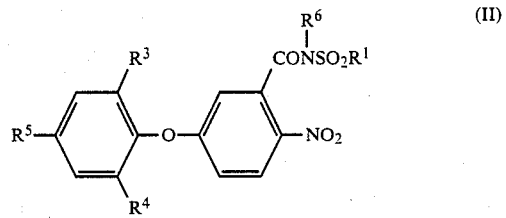

or a tautomer or salt thereof in substantially pure form wherein $R^1$ is $C_{1-6}$ alkyl optionally substituted by one or more halogen atoms; $R^3$ is hydrogen, fluorine, chlorine, bromine or iodine, $C_{1-6}$ alkyl, trifluoromethyl or a cyano group; $R^4$ is hydrogen, fluorine, chlorine, bromine, iodine or trifluoromethyl; $R^5$ is fluorine, chlorine, bromine, iodine or trifluoromethyl; and $R^6$ is hydrogen or $C_{1-4}$ alkyl; which process comprises nitrating a compound of formula (III):

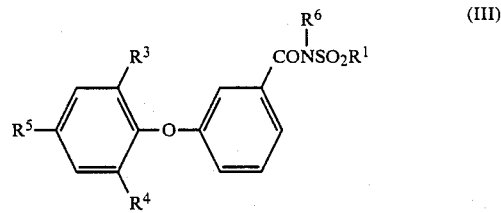

or a salt thereof wherein $R^1$, $R^3$, $R^4$, $R^5$ and $R^6$ are as defined above, in a solvent which is resistant to nitration under the desired reaction conditions and suitable for purification of the product of formula (II), heating the resultant solution to a temperature sufficient to at least partially dissolve the desired product and impurities and cooling the solution to precipitate the compound of formula (II) in substantially pure form.

10 Claims, No Drawings

CHEMICAL PROCESS

The present invention relates to a process for preparing certain herbicidal diphenyl ether derivatives.

EP-A-No. 22610 discloses a multi-stage process for preparing 2-nitro-5-(substituted phenoxy)benzoic acids and salts thereof which process includes nitration of the corresponding 5-(substituted phenoxy)benzoic acid.

European Pat. No. 3416 discloses diphenyl ether compounds of formula (I):

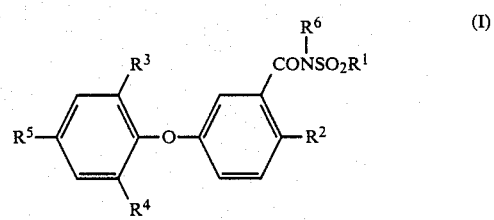

and tautomers and salts thereof; wherein $R^1$ is $C_{1-6}$ alkyl optionally substituted by one or more halogen atoms; $R^2$ is hydrogen, fluorine, chlorine, bromine or iodine or a nitro group; $R^3$ is hydrogen, fluorine, chlorine, bromine or iodine, $C_{1-6}$ alkyl, trifluoromethyl or a cyano group; $R^4$ is hydrogen, fluorine, chlorine, bromine, iodine or trifluoromethyl; $R^5$ is fluorine, chlorine, bromine, iodine or trifluoromethyl; and $R^6$ is hydrogen or $C_{1-4}$ alkyl. Salts of formula (I) are those formed by reacting a compound of formula (II) where $R^6$ is hydrogen with a base as described in EP No. 3416. Processes for the preparation of these compounds are also described.

The Applicants have found an improved process for preparing the compounds of formula (I) which is more efficient in term of the number of process steps required to obtain a substantially pure product. According to the present invention there is provided a process for preparing a compound of formula (II):

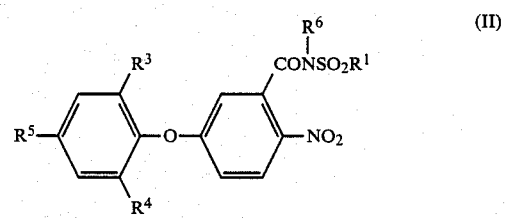

or a tautomer or salt thereof in substantially pure form wherein $R^1$, $R^2$, $R^3$, $R^4$, $R^5$ and $R^6$ are as hereinbefore defined in relation to formula (I); which process comprises nitrating a compound of formula (III):

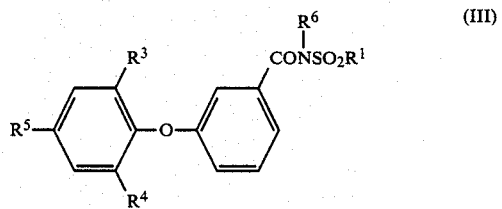

or a salt thereof wherein $R^1$, $R^3$, $R^4$, $R^5$ and $R^6$ are as hereinbefore defined in relation to formula (I); in a solvent which is resistant to nitration under the desired reaction conditions and suitable for purification of the product of formula (II), heating the resultant solution to a temperature sufficient to at least partially dissolve the desired product and impurities and cooling the solution to precipitate the compound of formula (II) in substantially pure form.

As used herein, the reference to a "salt" of formula (II) or (III) refer to the compounds obtained by reacting the appropriate compound where $R^6$ is hydrogen with a base to form a salt such as the sodium or potassium salt.

If necessary, water can be added to the reaction mixture during the final purification step in order to dilute any unreacted acid present.

Furthermore, it may be necessary to remove undissolved impurities by filtration prior to the final cooling step.

Suitably the nitration is effected by reaction with standard nitrating agent such as concentrated nitric acid, sodium nitrate, a mixture of concentrated sulphuric acid and sodium nitrate or a mixture of concentrated nitric cid and concentrated sulphuric acid.

Preferably a salt of the compound of formula (III) such as the potassium salt is used in the reaction.

Suitable solvents for use in the process include halogenated alkanes in particular chlorinated hydrocarbons such as dichloromethane, dichloroethene and dichloropropane in their various isomeric forms, chlorofluorohydrocarbons such as the Arctons, and aromatic solvents which are deactivated with respect to nitration such as nitrobenzene. The particular solvent employed will depend upon the solubility of the particular compound of formula (I) being prepared in it. The skilled chemist will be able to determine by routine procedures whether any specific solvent is appropriate for the nitration and purification steps.

The nitration step of the process is suitably carried out at moderate temperatures of from 0° C. to 40° C. and preferably at room temperature. The purification stages (heating, cooling and filtering) will depend upon the solvent and the compound of formula (I) being prepared.

Suitably the solution is heated to a temperature such a substantial proportion of impurties are dissolved for example more than 70% w/w. This will mean that at least partial dissolution of the product also takes place.

The water content of the reaction mixture is suitably controlled to an acceptable level. The precise content required for optimum results will depend upon a number of factors including, for example, the content of sulphuric acid present in the nitrating agents. Generally a water content of from 1%–3% w/w has been found to be acceptable. A convenient method of controlling the water content is to heat the solution to an appropriate temperature and remove water by distillation prior to adding the nitrating agent.

As used herein the expression "in substantially pure form" means that the product contains less than 10 % impurities, preferably less than 5 % impurities. Most preferably the product is substantially free of impurities.

Compounds of formula (III) and salts thereof are suitably prepared by reaction of a compound of formula (IV)

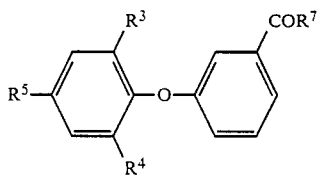 (IV)

wherein $R^3$, $R^4$ and $R^5$ are as hereinbefore defined in relation to formula (I) and $R^7$ is a leaving group such as halogen, in particular chlorine, with a compound of formula (V):

 (V)

wherein $R^1$ and $R^6$ are as hereinbefore defined in relation to formula (I) in the presence of a base, such as potassium carbonate.

In a preferred embodiment the reaction of the compound of formula (IV) with the compound of formula (V) is carried out in the same solvent as that used in the nitration and purification steps. This enables the compound salt of formula (III) to be reacted directly without first isolating it from solution.

Compound of formula (IV) and (V) are either known compounds or they can be prepared from known compounds by conventional methods.

Preferably the process of the invention is used to prepare a compound of formula (VI):

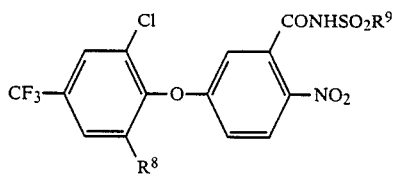 (VI)

wherein $R^8$ is hydrogen or fluorine and $R^9$ is methyl or ethyl. In the case where $R^8$ is hydrogen and $R^9$ is methyl, a preferred solvent for use in the above described process steps is 1,2-dichloroethane. When $R^8$ is fluorine and $R^9$ is ethyl, a preferred solvent is 1,2-dichloropropane.

The concentration of the reaction mixture in the solution can be varied at each stage in the process to the optimum for that stage by adding further solvent. For example in order to produce a compound of formula (VI) wherein $R^8$ is hydrogen and $R^9$ is methyl, the reaction of the appropriate compounds of formula (IV) and (V) is carried out at a concentration of about 28% w/w when the solvent is 1,2-dichloroethane. The resultant solution is preferably diluted to about 21% w/w by addition of further 1,2-dichloroethane in order to effect the nitration reaction. In this case, a nitrating agent comprising about 1.4 moles of the concentrated nitric acid to about 5 moles of concentrated sulphuric acid is added dropwise to the solution for every 1 mole of the compound of formula (III) present. Further 1,2-dichloroethane is preferably added to dilute the solution to about 15% w/w (excluding any added water) for the purification step. In this particular case the purification is carried out by heating the solution to about 70° 14 72° C. and then cooling in a controlled manner to 20° C.

It is possible to carry out the above-mentioned process steps in the same reaction vessel, although it may be more efficient to carry out every stage in a separate vessel as the solutions can readily be transferred from one vessel to another.

The following Examples illustrate the process.

EXAMPLE 1

This Example illustrates the preparation of the compound of formula:

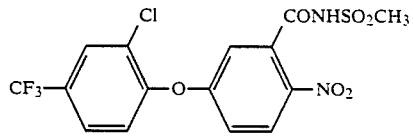

EXAMPLE 1A 1,2-dichloroethane (360ml) was charged into a 2l jacketed glass reactor, followed by methane sulphonamide (74.2g) and the temperature was raised to 50° C. Anhydrous potassium carbonate (210 g) was added with vigorous stirring and the reaction mixture was heated to reflux (83° C). 5-(2-chloro-4-trifluoromethylphenoxy)-benzoyl chloride (189.73 g) was added over a period of 1½ hours under reflux. The mixture was refluxed for a further 30 minutes, then water (420ml) added, and the temperature raised to 70° C., and maintained for a further ½ hour. The lower aqueous layer was separated off and the remaining upper layer was subjected to azeotropic distillation until a batch temperature of 77.5° C. was achieved which reduced the water content of the layer to approximately 3% w/w. Further 1,2-dichloroethane (230ml) was added and the resultant solution analysed, showing that it contained 21% w/w of 5-(2-chloro-4-trifluoromethyl-phenoxy)-N-methanesulphonylbenzamide and 2% w/w $H_2O$.

EXAMPLE 1B

A sample of the solution obtained in Example 1A (468.5g) was placed in a 500ml flask and a mixture of concentrated sulphuric acid (86.4g) and a mixture of a concentrated nitric acid (23.7g) and concentrated sulphuric acid (48.1 g) was added over a period of 2 hours with stirring, the temperature being maintained at 35° C. throughout. The reaction mixture was then allowed to cool to ambient temperature for 90 minutes after which water (370ml) and 1,2-dichloroethane (100 ml) were added. The mixture was heated under reflux (75° C.) for 30 minutes and allowed to cool to 20° C. overnight during which time solid product precipitated. The solid was filtered off, washed with water and dried at 80° C. to give the desired product (72g at 93% purity).

EXAMPLE 2

This Example illustrates the preparation of the compound of formula:

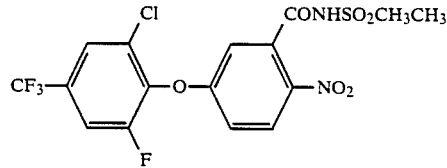

An aqueous solution (145.8g) of the potassium salt of 5-(2-chloro-6-fluoro-4-trifluoromethylphenoxy)-N-ethanesulphonylbenzamide (34.3g) was placed in a glass vessel and 1,2-dichloropropane (92.5g) added. The mixture was heated gradually to 70°–75° C. with stirring and 50% aqueous sulphuric acid was added dropwise until the pH of the aqueous phase was 1. The mixture was allowed to settle and the organic phase separated off.

A sample of the solution (130.6g) was placed in a 500ml flask and water (2.0g) added. Concentrated sulphuric acid (17.85 g) and a 1:2 mixture of concentrated nitric and sulphuric acid (35.7g) was added over a period of 2 hours with stirring, the temperature being maintained at from 25°–30° C. throughout. Stirring at 25°–30° C. was continued for a further ½ hour and then water (338g) was added and the mixture heated under reflux for 35 minutes. After self-cooling to 20° C., the mixture was allowed to stand at ambient temperature for two days. The solid precipitate thus formed was resuspended, filtered off and washed with water and dried at 60° C. to give the desired product (26.9g).

EXAMPLE 3

This Example illustrates the preparation of the compound of Example 1. A 25% w/w aqueous solution (400g) of the potassium salt of 5-(2-chloro-4-trifluoromethylphenoxy)-N-methanesulphonylbenzamide, 1,2dichloroethane (614 g) and a 1:2 mixture of concentrated nitric acid and concentrated sulphuric acid (21.2g) were placed in a reactor vessel and ortho-phosphoric acid (40g) added dropwise until the pH was 1.6. The mixture was heated to 70° C. and allowed to settle, after which the organic phase was separated off. The organic phase was heated to a temperature of 86° C., with azeotropic removal of water by distillation.

This solution (532.1 g) was placed in a reaction vessel and concentrated sulphuric acid (54 g) and a 1:2 mixture (52.35g) of concentrated nitric and concentrated sulphuric acid was added dropwise over a period of 1 hour 50 minutes during which time the temperature was maintained at 35° C. The mixture was then transferred to a separate vessel with the addition of 1,2-dichloroethane (12ml) and after stirring for 2 hours at 35° C., water (363g) was added. Following heating to a temperature of 73° C., the mixture was allowed to cool slowly to 27° C. whereupon the desired product was formed as a precipitate.

We claim:

1. A process for preparing a compound of formula (II):

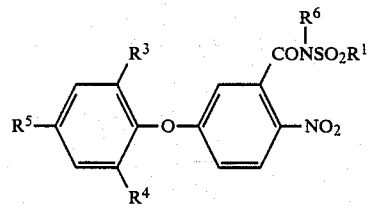

and tautomers and salts thereof in substantially pure form; wherein $R^1$ is $C_{1-6}$ alkyl optionally substituted by one or more halogen atoms; $R^3$ is hydrogen, fluorine, chlorine, bromine or iodine, $C_{1-6}$ alkyl, trifluoromethyl or a cyano group; $R^4$ is hydrogen, fluorine, chlorine, bromine, iodine or trifluoromethyl; $R^5$ is fluorine, chlorine, bromine, iodine or trifluoromethyl; and $R^6$ is hydrogen or $C_{1-4}$ alkyl; which process comprises nitrating a compound of formula III:

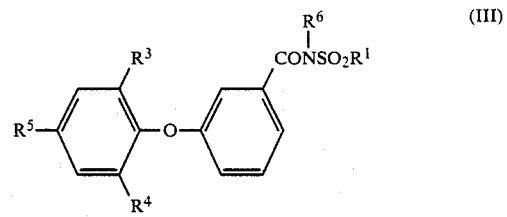

or a salt thereof wherein $R^1$, $R^3$, $R^4$, $R^5$ and $R^6$ are as defined above, with a nitrating agent in a solvent which is resistant to nitration under the desired reaction conditions and suitable for purification of the product of formula (II), heating the resultant solution to a temperature sufficient to at least partially dissolve the desired product and at least 70% w/w of impurities and cooling the solution to precipitate the compound of formula II in substantially pure form.

2. A process according to claim 1 wherein the said solvent is selected from halogenated alkanes, fluorohydrocarbons and aromatic solvents which are deactivated with respect to nitration.

3. A process according to claim 1 or claim 2 wherein a salt of a compound of formula (III) is employed in the process.

4. A process according to claim 1 wherein nitration is effected by reaction with a nitrating agent selected from concentrated nitric acid, sodium nitrate, a mixture of concentrated sulphuric acid and sodium nitrate or a mixture of concentrated nitric and sulphuric acids.

5. A process according to claim 1 for the preparation of a compound of formula (VI)

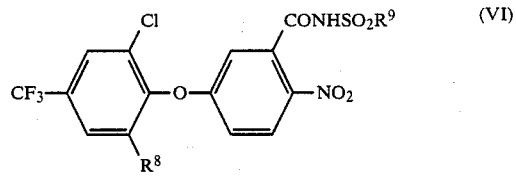

wherein $R^8$ is hydrogen or fluorine and $R^9$ is methyl or ethyl.

6. A process according to claim 5 wherein the compound of formula (VI) is one in which $R^8$ is hydrogen $R^9$ is methyl and the solvent is 1,2-dichloroethane.

7. A process according to claim 5 wherein the compound of formula (VI) is one in which $R^8$ is fluorine $R^9$ is ethyl and the solvent is 1,2-dichloropropane.

8. A process according to claim 1 wherein the compound of formula (III) is prepared by reacting a compound of formula (IV)

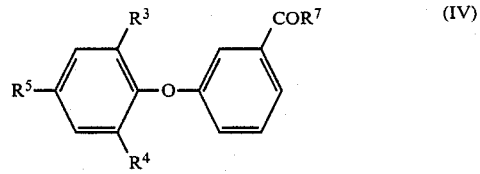

wherein $R^3$, $R^4$ and $R^5$ are as defined in claim 1; and $R^7$ is a leaving group; with a compound of formula (V)

(V)

wherein $R^1$ and $R^6$ are as defined in claim 1; in the presence of a base and in the said solvent.

9. A process according to claim 1 wherein the water content of the initial reaction mixture is adjusted to from 1% to 3% w/w.

10. A process according to claim 9 wherein the water content is controlled by heating the reaction mixture to an appropriate temperature and removing water by distillation prior to adding the nitrating agent.

* * * * *